US00PP27782P3

(12) United States Plant Patent
Ruter et al.

(10) Patent No.: US PP27,782 P3
(45) Date of Patent: Mar. 14, 2017

(54) ***ABUTILON* PLANT NAMED 'RUTABUT1'**

(50) Latin Name: *Abutilon×hybridum*
Varietal Denomination: RutAbut1

(71) Applicant: University of Georgia Research Foundation, Inc., Athens, GA (US)

(72) Inventors: John M. Ruter, Bishop, GA (US); Donglin Zhang, Athens, GA (US); Allan M. Armitage, Athens, GA (US); David A. Knauft, Watkinsville, GA (US); Suzzanne C. Tate, Athens, GA (US); Kelly Preslar, Signal Mountain, TN (US)

(73) Assignee: University of Georgia Research Foundation, Inc., Athens, GA (US)

( * ) Notice: Subject to any disclaimer, the term of this patent is extended or adjusted under 35 U.S.C. 154(b) by 59 days.

(21) Appl. No.: 14/545,198

(22) Filed: Apr. 6, 2015

(65) Prior Publication Data

US 2016/0295763 P1 Oct. 6, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — Klarquist Sparkman, LLP

(57) ABSTRACT

An *Abutilon* plant named 'RutAbut1' has full blooms throughout the summer, short internode lengths, and large flowers that are yellow-orange with a red throat.

2 Drawing Sheets

STATEMENT REGARDING FEDERALLY-SPONSORED RESEARCH

This invention was made, in part, with U.S. Government support on behalf of U.S. Department of Agriculture, Hatch Act Grant. The U.S. Government has certain rights in this invention.

Genus and species: *Abutilon×hybridum.*

Variety denomination: The new *Abutilon×hybridum* claimed is of the cultivar denominated 'RutAbut1'.

BACKGROUND OF THE INVENTION

The present invention relates to a new and distinct cultivar of *Abutilon×hybridum*, hereinafter referred to by the varietal denomination 'RutAbut1'.

Pedigree and history: The original 'RutAbut1' plant is a cross made between *Abutilon* 'Fairy Coral Red' (unpatented, female parent) and *Abutilon* 'Halo' (unpatented, male parent) in 2007 under the direction of David Knauft and Suzzanne Tate. Cuttings from the original 'RutAbut1' plant were first taken in Watkinsville, Ga. in March of 2008 and were planted in Watkinsville, Ga. in May of 2008 to produce asexually propagated plants of the new 'RutAbut1' variety. Additional plants of the 'RutAbut1' variety, asexually propagated by cuttings, were transferred to a location in Bonsall, Calif. in June of 2012 for further evaluation. 'RutAbut1' has been evaluated through trials at locations in Athens, Ga. from 2009 to 2013; in Tifton, Ga. from 2009 to 2012, in Bonsall, Calif. from 2012 to 2013; and in Watkinsville, Ga.

'RutAbut1' has been cold hardy outside in Athens, Ga. and Tifton, Ga. in unprotected containers sitting above ground. Flowering occurs on 'RutAbut1' from mid-April until hard frost in Athens, Ga., whereas most *Abutilon* selections stop flowering during the heat of summer.

The Inventors would expect the cultivar to be used commercially as a perennial in USDA zones 8-11. 'RutAbut1' can be used as a flowering annual in colder parts of the United States. Production is expected in the southeastern and southwestern United States. 'RutAbut1' should perform well in other countries with similar climates.

SUMMARY OF THE INVENTION

The following represent the distinguishing characteristics of the new *Abutilon* cultivar named 'RutAbut1'. In combination, these traits set 'RutAbut1' apart from all other existing varieties of *Abutilon* known to the inventor. Asexual propagation by cuttings has proven that these characteristics are firmly fixed in succeeding asexually propagated generations.

1. Full and blooms all through summer.
2. Shorter internodes.
3. Yellow orange flowers with a red throat.
4. Larger flowers.

Plants of the new 'RutAbut1' variety can be compared to 'Melon Sorbet' (unpatented) known in the industry. In comparison to 'Melon Sorbet', our new variety flowers more profusely. Melon Sorbet has orange outer petal color and no red throat.

Compared to its female parent 'Fairy Coral Red', 'RutAbut1' is more cold hardy, has more upright growth and larger flowers.

Compared to its male parent 'Halo', 'RutAbut1' has lighter a colored calyx and more yellow in the color of its petals.

TABLE 1

Flower sizes and color information for *Abutilon* varieties listed below; growing in a trial garden in Athens, Georgia (data were collected on Sep. 11, 2012).

| | Diameter (cm) | | Length (cm) | | |
|---|---|---|---|---|---|
| Clone | Mean | Range | Mean | Range | Note |
| 'A08-0401' | 3.4 | 2.9-3.7 | 3.8 | 3.5-4.0 | Bright red, stamens insert, heavy bloom. |
| 'RutAbut2' | 2.1 | 1.7-2.3 | 3.5 | 3.4-3.5 | Pure yellow, stamens exsert, only a few flowers |
| 'RutAbut1' | 2.9 | 2.2-4.0 | 3.2 | 2.6-3.5 | Yellow orange with red throat, stamens exsert, heavy to medium bloom |
| 'A08-2110' | 5.7 | 4.8-6.3 | 3.7 | 3.4-4.1 | Pinkish red (watermelon red), stamens exsert, medium bloom |
| 'A08-2112' | 6.0 | 4.8-6.8 | 3.9 | 3.4-4.3 | Red, stamens exsert, heavy bloom |
| 'A08-2114' | 5.7 | 4.9-6.1 | 3.8 | 3.6-4.1 | Yellow with distinguished red venation, stamens exsert, heavy bloom |
| 'A08-2121' | 2.9 | 2.2-3.8 | 3.9 | 3.2-4.7 | Light pinkish red, stamens insert, only a few flowers |
| 'A08-2125' | 5.5 | 4.5-6.1 | 4.4 | 4.0-4.6 | Yellow with red marginal veins, stamens exsert, heavy bloom |
| 'FCR' | 1.3 | 1.0-1.7 | 3.4 | 3.0-3.7 | Deep red, stamens exsert, only 3 flowers |
| 'A08-2131' | 5.4 | 4.5-6.2 | 3.7 | 3.4-4.2 | Pinkish red, stamens exsert, heavy bloom |

The above varieties are all unpatented. The A08 prefix designated clones and 'FCR' designation are experimental variety designations that may be changed at a later time. An application was filed for 'RutAbut2' on Apr. 6, 2015, and assigned U.S. Plant patent application Ser. No. 14/545,199.

BRIEF DESCRIPTION OF THE FIGURES

The accompanying colored photographic illustrations show the overall appearance and distinct characteristics of the new 'RutAbut1' cultivar. The colors in the photographs are as close as possible with the photographic and printing technology utilized.

The photograph labeled

The photograph labeled

DETAILED BOTANICAL DESCRIPTION

Figure 1:
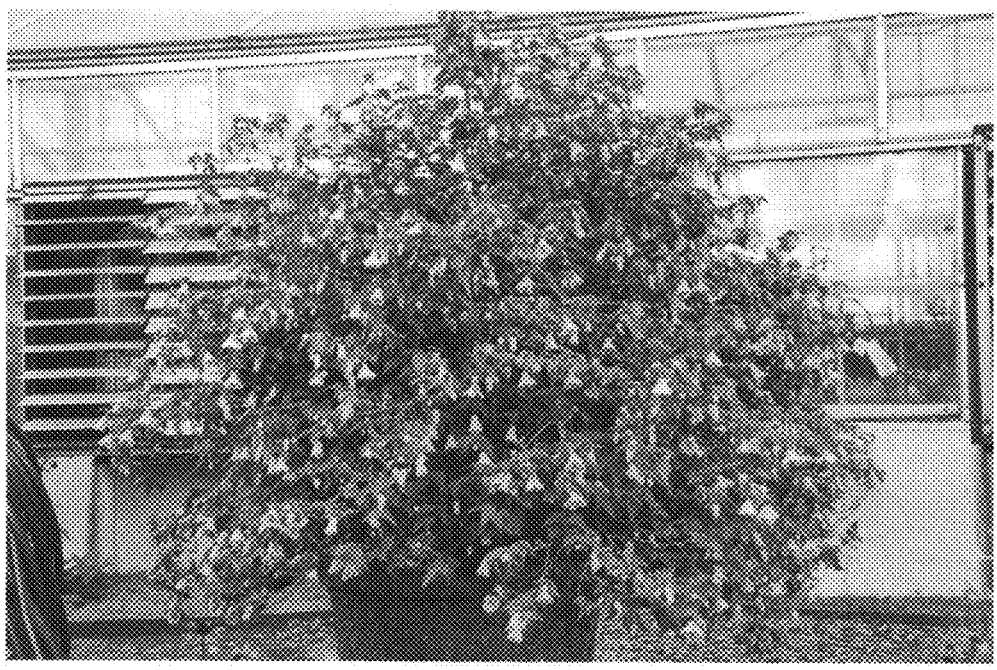
FIG. 1 depicts 'RutAbut1'.
Figure 2:
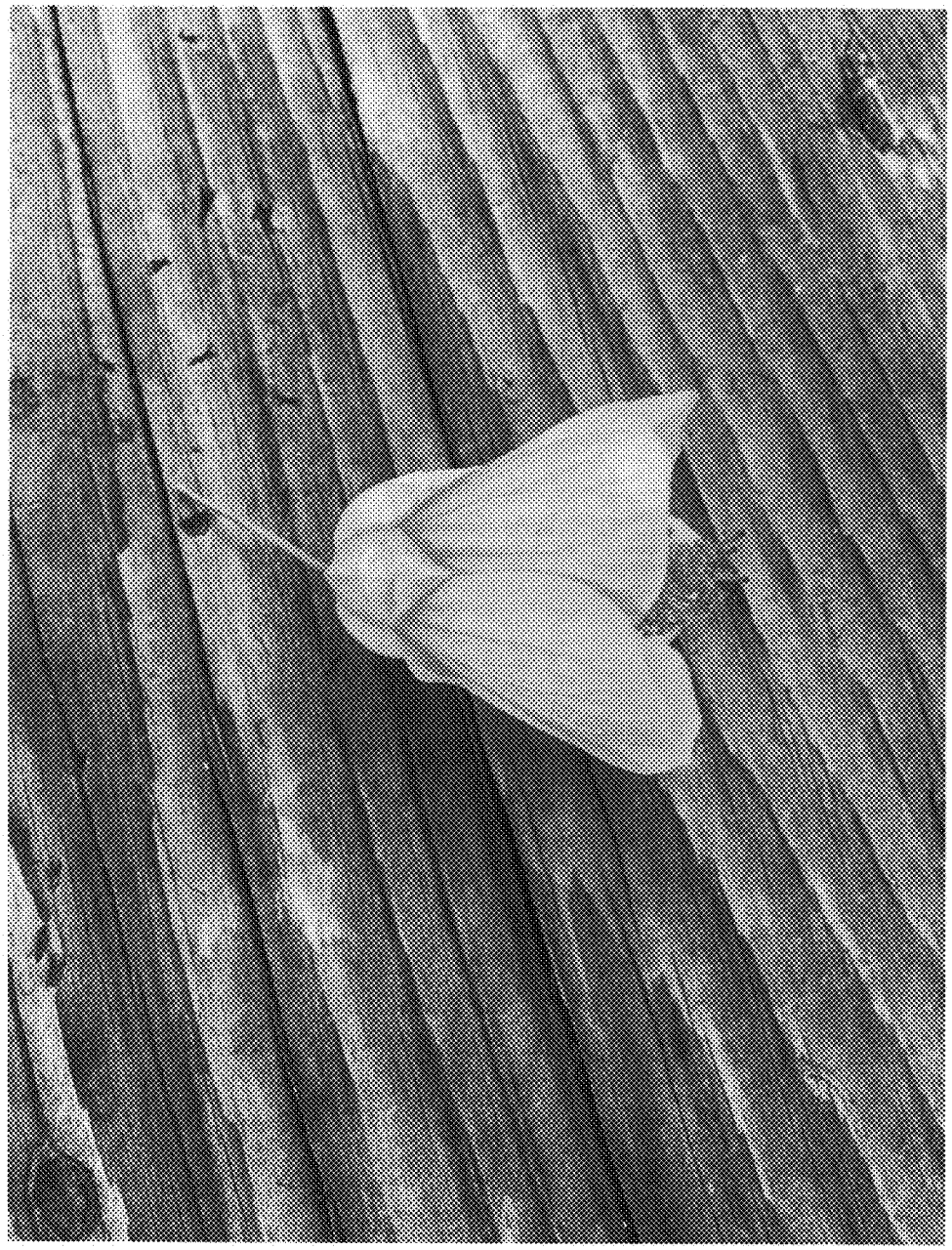
FIG. 2 depicts a flower from the plant of the new variety.

The following is a detailed description of the *Abutilon* cultivar named 'RutAbut1'. Data was collected in Tifton, Ga. from 12 month old plants grown from cuttings and growing outdoors in unprotected containers sitting above ground. 'RutAbut1' has not been tested under all possible conditions hence, phenotypic differences may be observed with variations in environmental conditions without any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society (R.H.S.), London, England.

Parentage: 'RutAbut1' is a seedling selection resulting from the deliberate controlled crossing of the following parents:

*Female parent*.—'Fairy Coral Red'.

*Male parent*.—'Halo'.

Vigor: Fairly vigorous.

Growth habit: Upright.

Type: Perennial in zones where it is hardy.

Size:

*Height* (*cm*).—130.

*Width* (*cm*).—110×150 — (typical, measurements taken at narrowest and widest widths).

Stems:

*Branching habit*.—Freely.

*Stem length* (*cm*) *typical range*.—7 to 48.

*Stem diameter* (*mm*) *typical*.—2.

*Stem texture*.—Smooth.

*Color*.—Green Group 143A.

*Pubescence*.—Yes.

*Shape*.—Round.

*Odor* (*of bruised stem*).—None.

*Internode length*.—2.5 cm.

Leaf:

*Upper color*.—Green Group, 139A.

*Lower color*.—Green Group, 139A.

*Mature size* (*L*×*W*) (*cm*).—11.4×8.

*Apex*.—Acuminate.

*Base*.—Cordate.

*Margin*.—Serrated.

*Shape*.—Lobed.

*Number of lobes*.—2 lobes per side.

*Pubescence*.—Present on both upper and lower leaf surfaces.

*Arrangement on stem*.—Alternate.

*Venation*.—Netted.

*Vein color, upper surface*.—Yellow-Green Group 147B.

*Vein color, lower surface*.—Yellow-Green Group 147C.

*Texture*.—Papery.

Petiole:

*Length* (*cm*).—7.

*Shape*.—Round.

*Color*.—Green Group 143A. Pubescence: Yes. Diameter (mm): 1.3. Stipules: none.

Flower:

*Inflorescence*.—Number of individual flowers per stem: generally one flower per leaf node.

*Individual flower*.—Size (L×W), typical, (cm): 3×3. Axillary or terminal: Axillary. Symmetry: Actinomorphic. Fragrance: None. Petal Number per flower: Five. Petal: Size (L×W), typical, (cm) — 3.2×2. Shape — spatular. Apex — round. Base — attenuate. Margin — entire. Color at peak of bloom — Upper: Orange Group 26B. Center: Red Group 46A.

*Petals*.—Not fused.

*Bud color*.—Greyed-Yellow 160A with Greyed-Red 179A along suture lines.

*Bud shape*.—Squared oval.

*Bud size* (*typical*).—Length (cm): 1.2. Width (cm at widest point): 1.

*Bud apex*.—Cuspidate.

*Bud surface*.—Heavily pubescent.

*Pedicels*.—Color — Green Group 143A. Pubescence — Yes. Length (cm) — 3.8.

*Sepals*.—Number — 5 calyx. Size(cm) — 1.5 length, 0.7 diameter. Shape — base connects, top divides. Pubescence — Yes. Color — Top: Greyed-Red 182B. Base: Yellow Green 151D.

*Stamens*.—Number — approximately 120. Size — 0.2 cm in length and 0.3 mm in diameter. Color — deep yellow with red filament. Pollen Color — Yellow-Orange group 17C. Pubescence — none. Anther color: Red Group 42A. Anther shape: Elliptical. Pollen quantity: Moderately heavy. Pollen color: Yellow-Orange Group 22A.

*Pistils*.—Size of style — length 3.4 cm. Color of style — Greyed-Purple 184D. Color of stigma — Greyed-Purple 185D.

Duration of bloom: In Watkinsville, Ga., individual flowers typically last about 5 days from bud opening.

Seed: None observed.

Hardiness: Proven hardy in USDA zones 8a and 10a where it has been grown and evaluated as of this time. Full range of USDA zones where the plant is hardy has not yet been determined.

Disease resistance: No unusual disease susceptibility or resistance has been observed to date.

What is claimed is:

1. A new and distinct cultivar of the *Abutilon×hybridum* plant named 'RutAbut1' substantially as illustrated and described herein.

* * * * *